United States Patent
Marvola et al.

[11] Patent Number: 5,962,024
[45] Date of Patent: Oct. 5, 1999

[54] PERORAL COMPOSITION FOR CONTROLLED RELEASE IN THE LOWER GASTROINTESTINAL TRACT

[75] Inventors: Martti Lauri Antero Marvola, Helsinki; Esko Veikko Marttila, Perttula; Reija Tuulikki Yrjölä, Ruutana; Esa Petteri Lahdenpää, Kallislahti, all of Finland

[73] Assignee: Orion-Yhtyma OY, Espoo, Finland

[21] Appl. No.: 08/913,554

[22] PCT Filed: Mar. 20, 1996

[86] PCT No.: PCT/FI96/00164

§ 371 Date: Dec. 2, 1997

§ 102(e) Date: Dec. 2, 1997

[87] PCT Pub. No.: WO96/29058

PCT Pub. Date: Sep. 26, 1996

[30] Foreign Application Priority Data

Mar. 21, 1995 [FI] Finland ................ FI951316

[51] Int. Cl.⁶ ................ A61K 9/26; A61K 9/30; A61K 9/58; A61K 9/62
[52] U.S. Cl. ................ 424/494; 424/458; 424/461; 424/462; 424/470; 424/474; 424/480; 424/482; 424/490; 424/497
[58] Field of Search ................ 424/474, 480, 424/490, 494, 470, 497, 461, 462, 482, 458, 487, 488

[56] References Cited

U.S. PATENT DOCUMENTS

5,209,933  5/1993  MacFarlane et al. ............ 424/494
5,525,354  6/1996  Posti et al. .................... 424/451

FOREIGN PATENT DOCUMENTS

393747   10/1990  European Pat. Off. .
440324   8/1991   European Pat. Off. .
92/16214 10/1992  WIPO .

OTHER PUBLICATIONS

Röhm Pharma, Prospekt, "Eudragit L und S, Anwendung in der Arzneimittel–Herstellung", 1984.

Yamada Akiya et al. (Teikoku Seiyaku KK), "Oral Administration Preparation for Treating Ulcerative Colitis and Crohn's Disease", PN JP3034928 —910214, Database Patent Abstracts of Japan, vol. 15, No. 163 (C–826), Apr. 24, 1991.

Teikoku Hormone MGF, "Oral Prepn. For Therapy of Ulcerous Colitis and Crohn's Disease—Contains 5–Aminosalicylic acid or Salazosulphapyridine", Disease WPI, AN 91–090637, Week 9113, Feb. 14, 1991, Derwent Publications Ltd., London, GB.

Sucker H. et al., "Pharmazeutische Technologie", 1991, 356–358, Thieme Verlag, Stuttgart.

*Primary Examiner*—Thurman K. Page
*Assistant Examiner*—James M. Spear
*Attorney, Agent, or Firm*—Finnegan, Henderson, Farabow, Garrett & Dunner, L.L.P.

[57] ABSTRACT

The invention relates to a peroral composition providing controlled release of a drug, the composition comprising a) a core comprising the drug and a drug release controlling agent and b) an enteric coating comprising the drug release controlling agent, wherein the drug release controlling agent consists substantially of a pH-sensitive enteric polymer. Preferably the pH-sensitive enteric polymer has a pH dissolving point of at least 6.5. The composition is preferably in the form of granules. Preferably, the composition is in the form of enteric matrix granules coated with an enteric coating. The composition releases the drug gradually in the lower gastrointestinal tract. The composition is especially suitable for the administration of 3-(3-cyanophenyl) methylene-2,4-pentanedione into the colon.

21 Claims, 1 Drawing Sheet

PERORAL COMPOSITION FOR CONTROLLED RELEASE IN THE LOWER GASTROINTESTINAL TRACT

This application is a 371 of PCI/FI96/00164 filed Mar. 20, 1996.

The invention relates to a composition intended for peroral intake, providing controlled drug release in the lower gastrointestinal tract. The composition according to the invention is especially well suited for the treatment of intestinal inflammations, especially inflammatory bowel diseases.

The invention relates in particular to a composition which is in granule form and releases phenylmethylene-2,4-pentanedione compounds in the lower gastrointestinal tract. Phenylmethylene-2,4-pentanedione compounds have been described previously in the applicant's patent application EP 440324. Animal test models have shown that these compounds, in particular 3-(3-cyanophenyl)methylene-2,4-pentanedione, have an effect in preventing intestinal inflammations, which effect is based specifically on local action on the inflamed intestinal wall. Phenylmethylene-2,4-pentanediones are thus useful in the treatment of, for example, ulcerative colitis and Crohn's disease, in which inflammation is present both in the small intestine and in the colon.

The object of the invention is to develop a composition which transports the drug to the lower gastrointestinal tract, where the drug is released gradually.

A further object is to develop a composition which releases the drug gradually in the lower gastrointestinal tract, where the drug acts locally in diseases of the lower gastrointestinal tract.

A particular object is to develop a composition which transports the drug at least to the lower part of the small intestine (ileum) before the drug begins to be released, and from which composition the drug is released gradually in the colon so that the entire drug dose has been released at the time the composition has reached the lower part of the colon.

The composition according to the invention may contain as the active agent any drug the release of which is desirable locally in the lower gastrointestinal tract, in particular in the colon. In addition to phenylmethylene-2,4-pentanediones the active agent may consist, for example, of other drugs used for the treatment of an intestinal inflammation, such as corticoids, 5-aminosalicylic acid and its derivatives. The active agent may also consist of drugs which act systemically. For example, the active agent may consist of drugs which have the chemical structure or polypeptides. Their peroral administration is limited by hydrolysis caused by digestive enzymes. The amount of these enzymes in the colon is, however, small, and so polypeptides can be absorbed satisfactorily also when administered perorally, insofar as the drug dosage form transports them as far as the colon before their release.

The composition according to the invention is a peroral composition providing controlled release of a drug, the composition comprising a) a core comprising the drug and a drug release controlling agent and b) an enteric coating, in which composition the drug release controlling agent substantially consists of a pH-sensitive enteric polymer.

The composition is preferably in the form of granules, preferably enteric matrix granules coated with enteric film. However, the formulation according to the invention may also be an enteric matrix tablet coated with enteric film.

The term "lower gastrointestinal tract" means here the lower part of the small intestine (ileum) and the colon. The term "enteric coating" means here a coating surrounding the core, the solubility of the coating being dependent on the pH in such a manner that it prevents the release of the drug in the stomach but permits the release of the drug at some stage after the formulation has emptied from the stomach. The term "pH-sensitive enteric polymer" respectively means a polymer the solubility of which is dependent on the pH so that it is insoluble in the gastric juice but dissolves at some stage after the formulation has emptied from the stomach. The term "pH dissolution point" means the pH value in which the pH-sensitive enteric polymer substantially begins to dissolve.

Of the agent used in the core for controlling drug release, about 95–100% by weight, preferably 99–100% by weight, most preferably 100%, consists of a pH-sensitive enteric polymer. The dissolving of the pH-sensitive enteric polymer must not begin until the lower part of the small intestine or the upper part of the colon. Thus the pH dissolution point of the pH-sensitive enteric polymer in the core must be higher than 6.0, preferably higher than 6.5, most preferably about 7. Suitable pH-sensitive enteric polymers include the various grades of hydroxypropylmethyl cellulose acetate succinate (HPMC-AS) sold under the trade name Aqoat, in particular Aqoat AS-HF, cellulose acetate phthalate (CAP), and methacrylic acid methylmethacrylate copolymer in which the ratio of free carboxylic groups to free ester groups is about 1:2 and which is sold under the trade name Eudragit S (molecular weigh about 135000). Additionally, the core may contain any fillers or lubricants possibly needed, such as calcium hydrogen phosphate, lactose, magnesium stearate, or talc. If the active agent is a polypeptide, the core may also contain absorption enhancing agents, such as salts of bile acids.

The enteric coating consists of a pH-sensitive enteric polymer, the dissolving of which must not begin until the lower part of the small intestine or in the upper part of the colon. In this case, the pH dissolving point of the polymer must be higher than 6.0, preferably higher than 6.5, most preferably about 7. Suitable pH-sensitive enteric polymers include the various grades of hydroxypropylmethyl cellulose acetate succinate (HPMC-AS) sold under the trade name Aqoat, in particular Aqoat AS-HF, cellulose acetate phthalate (CAP), an aqueous dispersion of which is sold under the trade name Aquateric, and methacrylic acid methyl methacrylate copolymer in which the ratio of free carboxylic groups to free ester groups is about 1:2 and which is being sold under the trade name Eudragit S (molecular weight about 135000). An especially suitable coating polymer is Aqoat AS-HF. Additionally, the coating may contain any excipients possibly needed, such as talc. The core and the coating may contain the same pH-sensitive enteric polymer.

The amount of enteric coating of the total weight of the formulation is about 10–50%, preferably 15–30%. The amount of the drug release controlling agent is about 0.1–20%, preferably 2–10%, of the weight of the core. The drug may be incorporated into the core in any suitable amount, which depends on the drug used and on the desired dosage. The amount of the drug in the core may be about 0.1–99%, preferably 1–90%, of the weight of the core. When the drug is 3-(3-cyanophenyl)-methylene-2,4-pentanedione, the amount of the drug in the core is about 10–95%, preferably 30–80%, of the weight of the core. A suitable daily dose of 3-(3-cyanophenyl)methylene-2,4-pentanedione for an adult is about 20–1000 mg, depending on the site of the inflammation being treated in the intestine, its degree and severity.

The core granules may be prepared by mixing the drug and any filler needed with each other and by granulating the mixture with an aqueous or ethanol solution of a suitable enteric polymer. The use of a water-free solvent is necessary if the active agent is sensitive to water. The granulation may be carried out by using known equipment, e.g. a blender granulator. After the granulation, the desired fraction is recovered by screening. The dimension of the core pellets may be about 0.1–3 mm, preferably about 0.5–2.0 mm.

The recovered matrix granules are coated, preferably by the fluidized bed technique. Other well known coating methods, such as a coating pan, may also be used. The coating solution is preferably an aqueous dispersion of an enteric polymer.

The coated granules may be administered to the patient as such, or preferably they are encased in a capsule, in which case the capsule contains an unit dosage of drug granules to be administered to the patient. If the formulation is an enteric matrix tablet coated with an enteric film, the core granules prepared in the manner described above may be pressed, possibly together with a filler, into a tablet by using a conventional tablet pressing machine, whereafter the tablet is coated with an ethanol solution or aqueous solution of an enteric polymer, for example by spray coating. Other methods known in the art may also be used for the preparation of an enteric matrix tablet.

The invention is illustrated by the following example compositions. In all of the examples the drug is; 3-(3-cyanophenyl)methylene-2,4-pentanedione.

|  |  | mg |
|---|---|---|
| Example 1. |  |  |
| Core: | Drug | 100.0 |
|  | Calcium hydrogen phosphate | 45.0 |
|  | Eudragit S | 5.0 |
| Coating: | Aqoat AS-HF | 40.0 |
| Example 2. |  |  |
| Core: | Drug | 100.00 |
|  | Calcium hydrogen phosphate | 45.0 |
|  | Aqoat AS-HF | 5.0 |
| Coating: | Aqoat AS-HF | 40.0 |
| Example 3.. |  |  |
| Core: | Drug | 100.00 |
|  | Calcium hydrogen phosphate | 45.0 |
|  | Eudragit S | 5.0 |
| Coating: | Aquateric (CAP) | 40.0 |
| Example 4. |  |  |
| Core: | Drug | 100.00 |
|  | Calcium hydrogen phosphate | 45.0 |
|  | Aqoat AS-HF | 5.0 |
| Coating: | Aquateric (CAP) | 40.0 |

The example compositions were prepared by granulating the drug and the filler with an ethanol solution of the enteric polymer by using a blender granulator and by recovering the 1.0–1.7 mm fraction of the core granules. The granules were coated by the fluidized bed technique using an aqueous dispersion of the coating polymer. In the example compositions the weight of the coating is about 20% of the weight of the final formulation, and in the core the weight of polymer is about 3.3% of the weight of the core. By using for the granulating a 20% ethanol solution of the polymer, it is possible by one wetting to obtain a polymer weight of about 2.5% of the weight of the core. By repeating the granulation it is possible to increase the weight of polymer to 6–7% of the weight of the core.

BRIEF DESCRIPTION OF THE DRAWINGS

Absorption tests Results, FIGURE I

In the absorption tests, model formulations were used in which 3-(3-cyanophenyl)methylene-2,4-pentanedione had been replaced with a corresponding amount of ibuprofen. Ibuprofen is a substance which is known to be absorbed from the entire intestinal tract, and therefore it is a usable model substance in an investigation of formulations which travel part of the way in the intestines without disintegrating.

Figure 1:
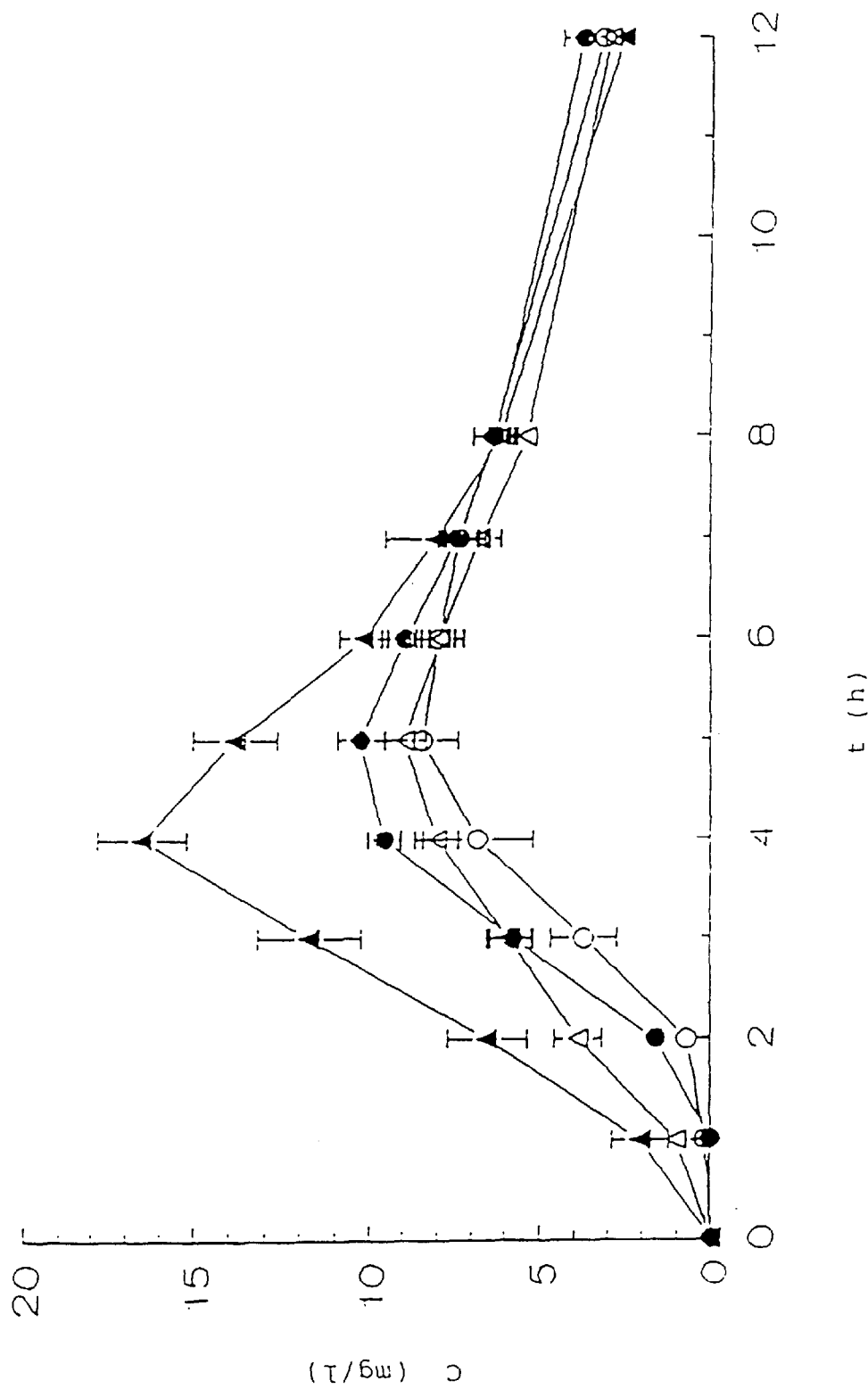
FIG. 1 shows the results of absorption tests carried out under fasting conditions with the four example compositions, the symbols meaning.

● As Example 1, but the drug being ibuprofen
○ As Example 2, but the drug being ibuprofen
▲ A As Example 3, but the drug being ibuprofen
Δ A As Example 4, but the drug being ibuprofen In fasting conditions it can be calculated that the emptying of the pellets from the stomach takes approximately one hour and their travel through the small intestine three hours At four hours the granules are thus in the lower part of the small intestine or the upper part of the colon. With three of the four formulations it is observed that clearly more than one-half of the area of the concentration/time curve is after four hours. Most of the drug dose has thus been released after this time. In conformity with tests in vitro, the release is delayed and prolonged most by a combination in which both the matrix polymer and the coating are Aqoat AS-HF. An Aquateric film disintegrates clearly more rapidly.

We claim:

1. A peroral controlled release composition, wherein said composition releases a drug substantially in a colon, said composition comprising a) a core comprising said drug and a drug release controlling agent and b) an enteric coating comprising said drug release controlling agent, wherein said drug release controlling agent consists substantially of a pH-sensitive enteric polymer, wherein said pH-sensitive enteric polymer has a pH dissolving point of at least 6.5.

2. The composition according to claim 1, wherein about 95–100% by weight of said drug release controlling agent consists of said pH-sensitive enteric polymer.

3. The composition according to claim 2, wherein 99–100% by weight of said drug release controlling agent consists of said pH-sensitive enteric polymer.

4. The composition according to claim 3, wherein 100% by weight of said drug release controlling agent consists of said pH-sensitive enteric polymer.

5. The composition according to claim 1, wherein the amount of said coating is 10–50% by weight of the total weight of said composition.

6. The composition according to claim 5, wherein the amount of said coating is 15–30% by weight of the total weight of said composition.

7. The composition according to claim 1, wherein the amount of said drug release controlling agent in said core is 1–20% by weight of the weight of said core.

8. The composition according to claim 7, wherein the amount of said drug release controlling agent in said core is 2–10% by weight of the weight of said core.

9. The composition according to claim 1, wherein said drug comprises a phenylmethylene-2,4-pentanedione structure.

10. The composition according to claim 9, wherein said drug is 3-(3-cyanophenyl)methylene-2,4-pentanedione.

11. The composition according to claim 1, wherein said composition is in the form of a granule.

12. The composition according to claim 1, wherein said composition is in the form of a tablet.

13. The composition according to claim 1, wherein said core comprises a homogenous mixture of said drug and said drug release controlling agent.

14. The composition according to any one of claims 1–13, wherein said pH-sensitive enteric polymer has a pH dissolving point of about 7.

15. The composition according to claim 14, wherein said pH-sensitive enteric polymer is hydroxypropylmethyl cellulose acetate succinate (HPMC-AS) or methacrylic acid methyl methacrylate copolymer, wherein the ratio of free carboxylic groups to free ester groups in said methacrylic acid methyl methacrylate copolymer is about 1:2.

16. A method for preparing a peroral controlled release composition, wherein said composition releases a drug substantially in a colon, wherein said method comprises granulating said drug with a water-free solution of a pH-sensitive enteric polymer, wherein said pH-sensitive enteric polymer has a pH dissolving point of at least 6.5, screening a desired fraction of the resulting granules, and coating said granules with a coating comprising a pH-sensitive enteric polymer, wherein said pH-sensitive enteric polymer has a pH dissolving point of at least 6.5.

17. The method according to claim 16, wherein said drug is mixed with a filler before granulating.

18. The method according to claim 16 or 17, wherein said pH-sensitive enteric polymer has a pH dissolving point of about 7.

19. A method for preparing a peroral controlled release composition, wherein said composition releases a drug substantially in a colon, wherein said method comprises granulating said drug with a water-free solution of a pH-sensitive enteric polymer, wherein said pH-sensitive enteric polymer has a pH dissolving point of at least 6.5, screening the desired fraction of the resulting granules, pressing said granules into a tablet, and coating said tablet with a coating comprising a pH-sensitive enteric polymer, wherein said pH-sensitive enteric polymer has a pH dissolving point of at least 6.5.

20. The method according to claim 19, wherein said drug is mixed with a filler before granulating.

21. The method according to claim 19 or 20, wherein said pH-sensitive enteric polymer has a pH dissolving point of about 7.

\* \* \* \* \*